United States Patent [19]

Moberg et al.

[11] Patent Number: 5,650,843
[45] Date of Patent: Jul. 22, 1997

[54] FEEDBACK CONTROL APPARATUS FOR A LIGHT INTEGRATING CAVITY

[75] Inventors: Gregory Oscar Moberg, Rochester; Allen Davenport Bellinger, Webster; Jeffrey George Weber, Rochester, all of N.Y.

[73] Assignee: Eastman Kodak Company, Rochester, N.Y.

[21] Appl. No.: 655,654

[22] Filed: May 30, 1996

[51] Int. Cl.⁶ ........................................... G01J 1/42
[52] U.S. Cl. .................... 356/236; 250/205; 250/228
[58] Field of Search ............... 356/236; 250/205, 250/228

[56] References Cited

U.S. PATENT DOCUMENTS

| | | | |
|---|---|---|---|
| 4,321,630 | 3/1982 | Kramer | 358/294 |
| 4,725,893 | 2/1988 | Granger | 358/294 |
| 4,810,937 | 3/1989 | Havel | 315/152 |
| 4,868,383 | 9/1989 | Kurtz et al. | 250/228 |
| 5,018,019 | 5/1991 | Moore | 358/215 |
| 5,164,586 | 11/1992 | Hohberg et al. | 250/226 |
| 5,164,844 | 11/1992 | Granger | 258/474 |
| 5,241,459 | 8/1993 | Kaplan et al. | 250/228 |

*Primary Examiner*—Richard A. Rosenberger
*Attorney, Agent, or Firm*—Francis H. Boos, Jr.

[57] ABSTRACT

Feedback control of a spatially distributed light source for a light integrating cavity in which the light acceptance angle of the light feedback device is expanded by means of a light diffuser at the feedback port so as to better average the localized light intensity variations on the internal surface area of the cavity caused by arc wander in the spatially distributed light source.

9 Claims, 3 Drawing Sheets

5,650,843

FEEDBACK CONTROL APPARATUS FOR A LIGHT INTEGRATING CAVITY

FIELD OF THE INVENTION

The invention relates generally to the field of light illumination sources using an integrating cavity to produce a diffuse light output for film scanning and more specifically to the use of feedback to control the uniformity of the diffuse light output from the cavity when utilizing a spatially distributed light source as input to the cavity.

BACKGROUND OF THE INVENTION

The use of a linear integrating cavity as part of an illuminator for a photographic film scanner is well known. A basic integrating cavity has a cylindrical cavity comprising an interior white diffusing surface of high reflectivity, a light entry port and a light exiting slot. Light from an external source is input into the cavity through the entry port. The light is scattered throughout the cavity and exits through the slot to provide uniform diffuse light for exposure to the photograhic film in the scanner. Commonly assigned U.S. Pat. No. 5,241,459, the disclosure of which is incorporated herein by reference, describes such a cavity in an illuminator system that is also provided with a feedback port for the sampling of light within the cavity. This light sample is conveyed via a fiber optic cable to a detector and automatic control circuit. The output of the automatic control circuit is coupled back to the light source to control the light source so as to avoid fluctuation in the intensity of the light beam entering the cavity.

In such illuminator system using feedback control for the light source, it has been found that in some cases the intensity of the light exiting the slot varies even though the feedback controls are working properly. The problem appears to occur primarily when the input light source is spatially distributed, as in the case of a xenon arc lamp, for example, in which the spatially distributed arc moves in a manner commonly referred to as "arc wander". There is therefore a need for feedback control in a light integrating cavity type of illuminator system utilizing a spatially distributed light source that is immune to effects of arc wander in the light source.

SUMMARY OF THE INVENTION

To this end, there is provided feedback control apparatus for an illuminator system of the type having a light integrating cavity with a light input port, a slot for emitting diffuse integrated light and a feedback port for providing a sample of integrated light from within the cavity, an arc lamp light source for injecting light into the cavity, the arc being subject to motion, and feedback control means including a fiber optic cable optically coupled to the feedback port for controlling the intensity of light into the cavity to maintain stable light intensity within the cavity, the fiber optic cable having a narrow light acceptance angle which intercepts integrated light from a relatively small radiating surface area within the cavity. In accordance with a feature of the invention, the feedback control means includes means for substantially expanding the light acceptance angle of the cable at the optical coupling of the fiber optic cable to the feedback port. In one embodiment, such expanding means comprises a light diffuser element inserted into the feedback port between the interior cavity surface and the end of the fiber optic cable. It is believed that an effect of the arc wander in the light source is to cause localized variations of light intensity on the interior surface of the integrating cavity. These are captured by the unmodified fiber optic feedback cable and cause the control apparatus to vary the light source intensity, the result being to inject compensatory control of light intensity when none is needed. The effect of the light diffusion means is to expand the area of the cavity interior surface seen by the fiber optic cable thereby providing a more integrated light to the feedback control apparatus and avoiding the effect of localized light intensity variations caused by arc wander in the light source. As an alternative to the light diffuser element, the expanded acceptance angle may comprise an end section of the fiber optic cable in which the individual optical fibers are splayed outwardly to increase the overall acceptance angle of the cable. In another embodiment, an elongated section of the exit port between the point of opening into the cavity interior and the end of the fiber optic cable is provided with a surface of high reflectivity to provide for secondary light integration from an expanded interior surface area of the cavity as seen by the opening of the exit port.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Figure 1:
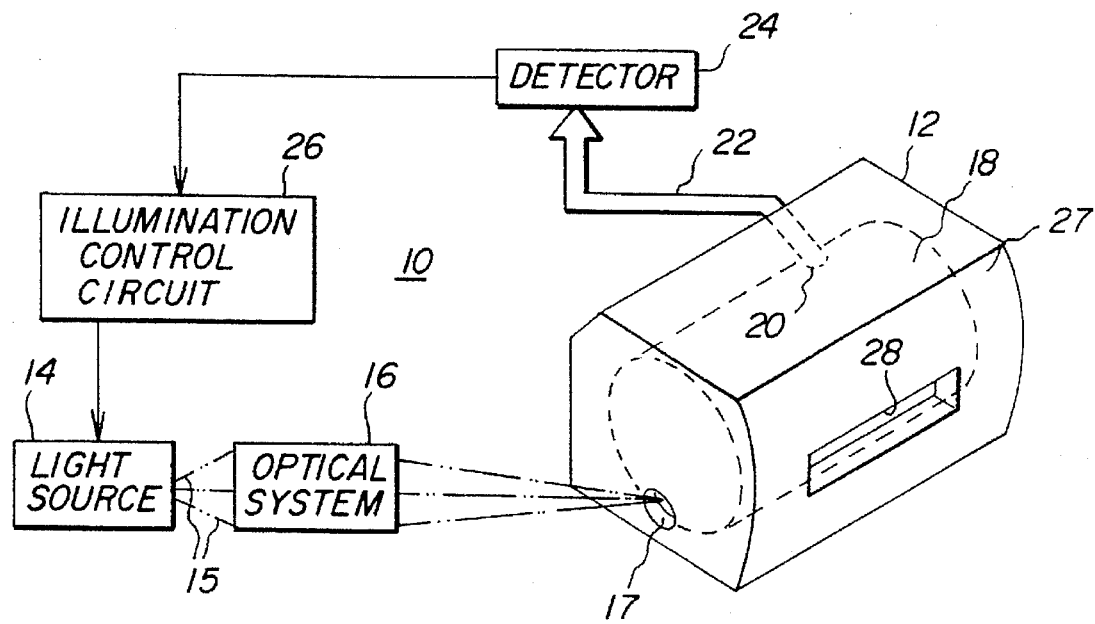
FIG. 1 is a a view in perspective of an illuminating system embodying an integrating cylinder and a light feedback system with which the present invention is particularly useful.

Referring now to FIG. 1, there is shown an illuminator system 10 for a film scanner. The illuminator system includes an integrating cylinder 12, a light source 14, and an optical system 16 for directing light rays 15 from source 14 at an angle through a light input port 17 into the interior cavity 18 of cylinder 12. A feedback port 20 receives a fiber optic cable 22 for sampling light from within the cavity. The cable is coupled to a detector 24 (e.g. photocell) where the light sample is converted to an electrical signal which is fed to an illumination control circuit 26, the output of which is coupled to light source 14 for the purpose of controlling and substantially avoiding fluctuation in the intensity of the light beam 15. The internal surface of the cavity 18 is highly reflective to enhance the integration of the light within the cavity. The high reflectivity may be achieved using various techniques. For example, the integrating cylinder 12 may be made of a metal such as aluminum and hollowed out to form the cavity 18 which is then coated with a high reflectivity material, such as a white reflective paint. Alternatively, the integrating cylinder can be machined from a non-metallic matierial such as white Tefleon to directly provide the highly reflective surface. One outer side 27 of the integrating cylinder 12 is curved to accomodate the passage thereover of a film being scanned and is provided with an elongated slot 28 for exposure of the integrated light within cavity 18 to the film being scanned.

Figure 2:
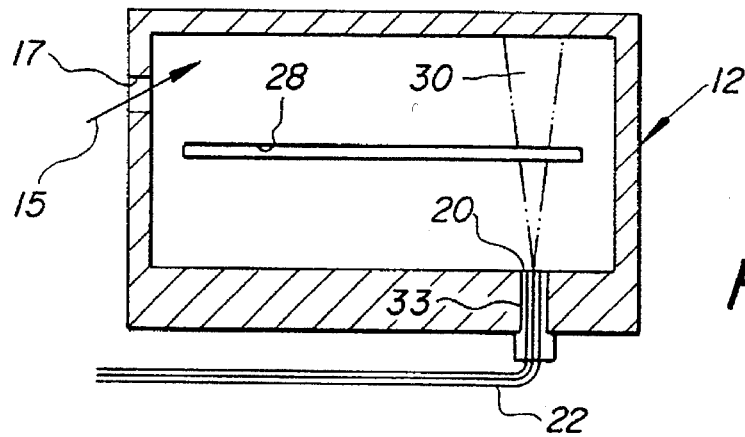
FIG. 2 is a plan view in cross section of the integrating cylinder of FIG. 1 illustrating a prior art form of light feedback apparatus.
Figure 3:
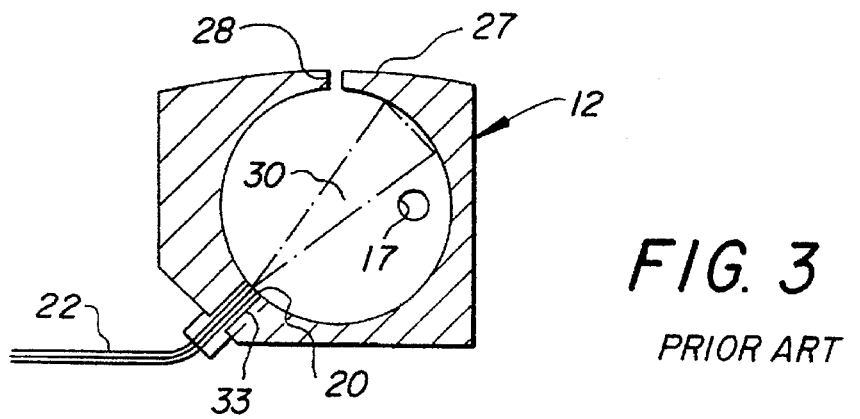
FIG. 3 is an end view in cross section of the integrating cylinder of FIG. 1 illustrating the prior art form of light feedback apparatus.

In FIGS. 2 and 3 there are shown schematic cross sectional views of the integrating cylinder in which the shaded region 30 represents the solid angle of acceptance of the fiber optic cable 22 from which light samples are derived from the internal cavity in accordance with prior art practice. In general, the angle of acceptance is relatively narrow, on the order of 15° which results in the light sample for feedback control purposes being taken from a relatively small region on the cavity internal surface. As long as the intensity of light reflected from this limited surface area varies only with overall light intensity entering cavity 18 from the light source 14, the light sample communicated back through cable 22 to detector 24 and control ciruict 26 will accurately represent any variations in the overall light intensity and can be used effectively to provide feedback control of the light intensity from light source 14. However, it has been found unexpectedly that when using spatially varying illumination sources, such as xenon arc lamps, the integrated light intensity emitted through slot 28 varies despite the fact that feedback control is in operation. It is believed that this phenomenon is caused by the fact that Spatially varying illumination sources of the type described are subject to arc wander which appears as "flicker" in the light source. When applied to an integrating cylinder to produce diffuse light, the spatial distribution of the cylinder input light is averaged out as the cylinder integrates and the effects of the arc wander do not significantly affect the diffuse light output from the exit slot 28. However, the light averaging to the feedback port as "seen" by the fiber optic cable from the limited surface area within the cable's acceptance angle is not the same as it is at the exit slot 28 and results in a false feedback which introduces unwanted flicker in the diffuse light at the slot 28 through the action of control circuit 26.

Figure 4:
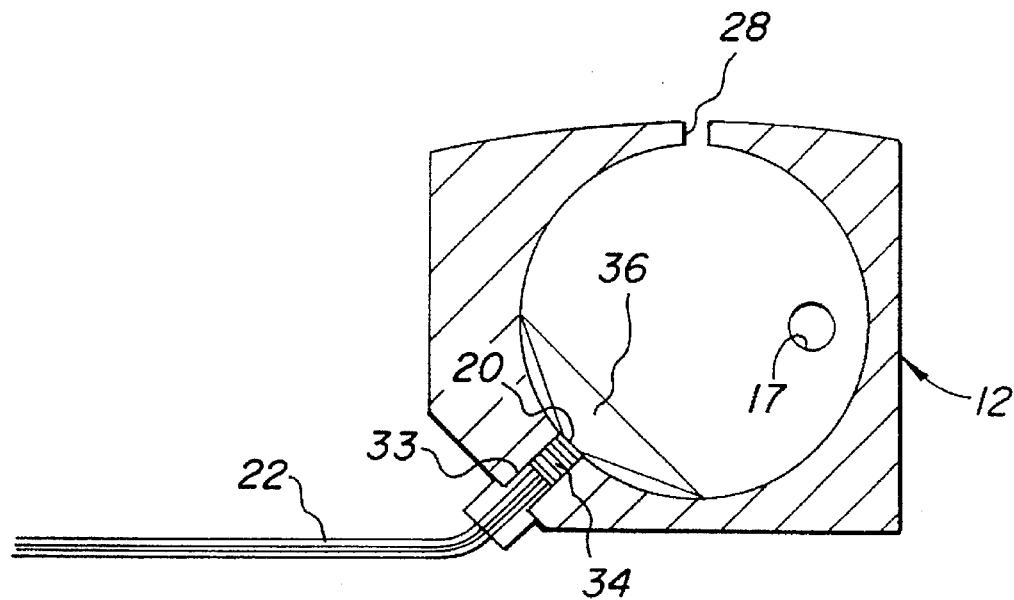
FIG. 4 is an end view of the integrating cylinder of FIG. 1 illustrating one embodiment of the light feedback apparatus of the present invention.

It has been found in accordance with the present invention that the flicker in the diffuse output light can be substantially reduced or eliminated by substantially expanding the effective light acceptance angle of the cable at the optical coupling of the fiber optic cable to the feedback port. In the embodiment illustrated in FIG. 4, this is accomplished by inserting a light diffusing member 34 within the bore hole 33 which defines the feedback port 20 so that the light acceptance angle is substantially broadened as shown by the shaded region 36. The effect of this is to provide a sample of integrated light that is more nearly akin to the diffuse integrated light emitted from exit slot 28 and which is substantially free from localized flicker caused by the arc wander in the spatially distributed light source 14. A lucite cylindrical rod having both ends bead blasted to provide the required diffusing action may be used for the light diffusing element.

Figure 5:
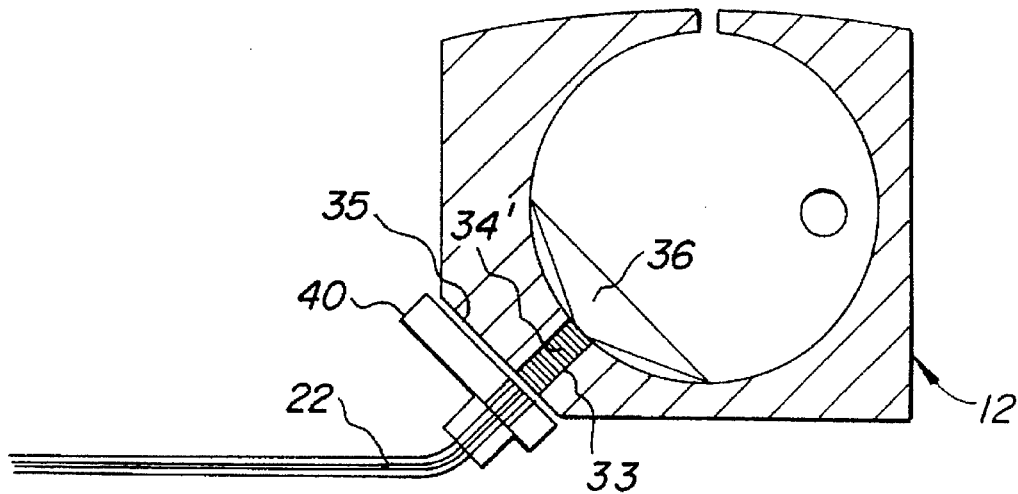
FIG. 5 is an end view similar to FIG. 4 illustrating another embodiment of the light feedback apparatus in accordance with the invention.

In FIG. 5 an alternative embodiment is shown in which an extended light diffusing element 34' is inserted within bore hole 33 so as to extend entirely through the bore hole from the feedback port 20 to the cylinder outer surface 35. This allows the end coupler 40 of the fiber optic cable tap to be separate from the integrating cylinder rather than being coupled into the cylinder feedback port bore hole. This is an advantage in scanner maintenance since it allows the integrating cylinder 12 to be removed from its mounting and replaced without disturbing the fiber optic cable coupling 40.

Figure 6:
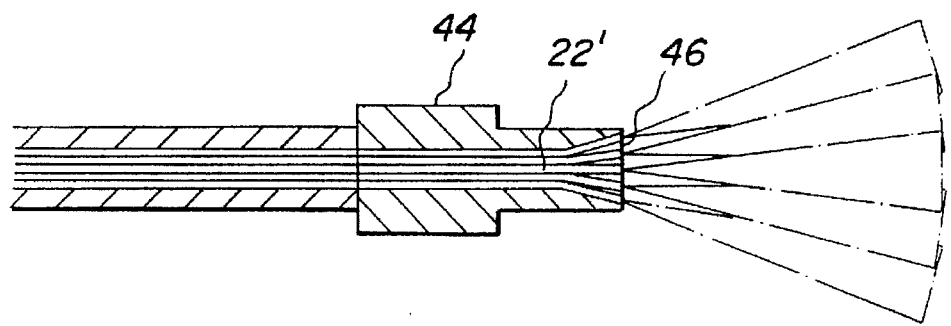
FIG. 6 is a diagrammatic illustration of a fiber optic cable useful in accordance with yet another embodiment of the light feedback apparatus of the present invention.
Figure 7:
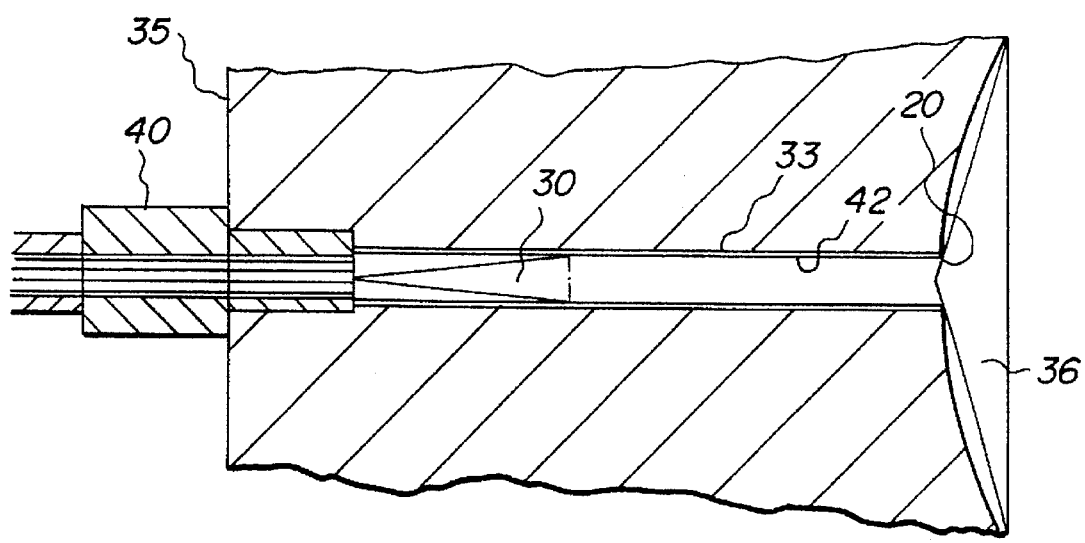
FIG. 7 is a diagrammatic illustration of a portion of an integrating showing a further embodiment of the light feedback apparatus of the present invention.

Another arrangement for expanding the acceptance angle is seen in FIG. 6. In this arrangement, the bundle of optical fibers 22' are splayed outwardly at the end of the coupler 44 so that the overall acceptance angle of the cable is expanded by the fanning out of the individual fibers. A suitable filler 46 may be injected into the interstices between the fiber ends to hold the fibers in the splayed mode. In yet another embodiment illustrated in FIG. 7, the bore hole 33 leading from the feedback port 20 to the outer surface 35 is provided with a surface of high reflectivity 48, preferably in the same manner as described above in regard to the interior surface of the integrating cavity. In the example of FIG. 7, the fiber optic cable is shown inserted partially into the bore hole 33 although it may also be terminated at an external coupler such as shown in FIG. 5. Integrated light from the widened acceptance angle 36 enters through the feedback port 20 and is reflected multiple times before reaching the fiber optic cable. The effect is to perform light integration from a surface area within the cavity that is significantly expanded beyond the relatively narrow acceptance angle of the fiber optic cable itself.

The invention has been described with reference to a preferred embodiment. However, it will be appreciated that variations and modifications can be effected by a person of ordinary skill in the art without departing from the scope of the invention.

Parts List 10 illuminator system
12 integrating cylinder
14 light source
15 light rays
16 optical system
17 light input port
18 interior cavity of cylinder
20 light feedback port
22 fiber optic cable
24 detector
26 illumination control circuit
28 diffuse light output slot
30 angle of acceptance
33 bore hole
34 light diffusing element
35 exterior surface of cylinder
36 widened acceptance angle
40 fiber optic end coupler
42 high reflectivity surface

What is claimed is:

1. Feedback control apparatus for a light integrating cavity system including a light integrating cavity having a light input port, a slot for emitting integrated light and a feedback port for providing a sample of integrated light within the cavity, an arc lamp light source for injecting light into the cavity, the arc being subject to motion, and feedback control means including a fiber optic cable optically coupled to the feedback port for controlling the intensity of light into the cavity to maintain stable light intensity within the cavity, the fiber optic cable having a narrow light acceptance angle which intercepts integrated light from a relatively small radiating surface area within the cavity, in combination therewith:

means for substantially expanding the light acceptance angle of the cable at the optical coupling of the fiber optic cable to the feedback port.

2. The apparatus of claim 1 wherein said fiber optic cable comprises a bundle of discrete optical fibers and said light expanding means comprises an end section of the cable in which the fibers are splayed to create an expanded light acceptance angle.

3. The apparatus of claim 2 wherein said end section includes a filler interposed between adjacent optical fibers to maintain the fibers in a splayed condition.

4. The apparatus of claim 1 wherein said light expanding means includes a light diffuser positioned in the feedback port between the cavity and the fiber optic cable.

5. The apparatus of claim 1 wherein said light expanding means comprises an elongated section of feedback port between the cavity and the fiber optic cable, the elongated section having a high reflectance surface to effect secondary integration of light entering the feedback port from a wide angle of acceptance of light from within the cavity.

6. A light feedback controlled integrating cavity system comprising:

an arc lamp source subject to arc wander;

a light integrating cavity having a light input port for receiving light from the arc lamp, a high reflectance interior surface, a light output slot for projecting a uniform integrated linear diffuse light from the cavity and a light feedback port;

feedback control means for maintaining constant intensity integrated light at the light output slot, said feedback control means including a fiber optic cable coupled to the feedback port for obtaining a light sample from inside the cavity, said cable having a defined light input acceptance angle; and light diffusing means effective at the coupling of the fiber optic cable to the feedback port to expand the sampled surface area of the cavity substantially beyond the area defined by the acceptance angle of the fiber optic cable;

whereby localized fluctuations in feedback light within the integrating cavity caused by arc wander are substantially reduced upon reflection into the fiber optic cable.

7. The system of claim 6 wherein said feedback port has a first end open to the light integrating cavity and said light diffusing means comprises a light diffusing element positioned at least partially within said feedback port at said first end to accept light from an acceptance angle significantly greater than the acceptance angle of the fiber optic cable.

8. The system of claim 6 wherein said feedback port has a first end open to the light integrating cavity, said fiber optic cable comprises a bundle of discrete optical fibers and said light expanding means comprises an end section of the cable in which the fibers are splayed to create an expanded light acceptance angle.

9. The system of claim 6 wherein said light diffusing means comprises an elongated section of said feedback port between the cavity and the fiber optic cable, the elongated section having a high reflectance surface to effect secondary integration of light entering the feedback port from a wide angle of acceptance of light from within the cavity.

* * * * *

UNITED STATES PATENT AND TRADEMARK OFFICE
CERTIFICATE OF CORRECTION

PATENT NO. : 5,650,843
DATED : July 22, 1997
INVENTOR(S) : Gregory O. Moberg, et al It is certified that error appears in the above-identified patent and that said Letters Patent is hereby corrected as shown below:

Cover Page -- U.S. Provisional Application No. 60/005,628, filed 19 October 1995 --

Column 1, Line 3 -- CROSS REFERENCE TO RELATED APPLICATION; Reference is made to and priority claimed from U.S. Provisional Application Serial No. 60/005,628, filed 19 October 1995, entitled FEEDBACK CONTROL SYSTEM FOR AN OPTICAL INTEGRATING CYLINDER --

Signed and Sealed this

Thirtieth Day of December, 1997

Attest:

BRUCE LEHMAN

Attesting Officer

Commissioner of Patents and Trademarks